(12) United States Patent
Baumgartner

(10) Patent No.: US 9,173,715 B2
(45) Date of Patent: Nov. 3, 2015

(54) ULTRASOUND CT REGISTRATION FOR POSITIONING

(75) Inventor: Adrian Baumgartner, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 142 days.

(21) Appl. No.: 13/523,035

(22) Filed: Jun. 14, 2012

(65) Prior Publication Data

US 2013/0150709 A1 Jun. 13, 2013

Related U.S. Application Data

(60) Provisional application No. 61/499,838, filed on Jun. 22, 2011, provisional application No. 61/499,849, filed on Jun. 22, 2011.

(51) Int. Cl.
*A61B 19/00* (2006.01)
*A61B 17/88* (2006.01)
(Continued)

(52) U.S. Cl.
CPC . *A61B 19/46* (2013.01); *A61B 6/12* (2013.01); *A61B 17/88* (2013.01);
(Continued)

(58) Field of Classification Search
CPC .... A61B 17/88; A61B 17/8866; A61B 19/46; A61B 19/5244; A61B 2019/5251; A61B 2019/5263; A61B 2019/5276; A61B 2019/5287; A61B 2019/5289; A61B 2019/5416; A61B 2019/5445; A61B 2019/5454; A61B 2019/547; A61B 6/12; G06T 7/0024; G06T 7/0028; G06T 2207/30008

USPC .......... 600/424, 425, 437; 382/128, 291; 606/102, 97

See application file for complete search history.

(56) References Cited

U.S. PATENT DOCUMENTS

| 5,636,255 A | 6/1997 | Ellis |
| 6,436,100 B1 | 8/2002 | Berger |

(Continued)

FOREIGN PATENT DOCUMENTS

| CN | 1950849 | 4/2007 |
| CN | 101305395 | 11/2008 |

(Continued)

OTHER PUBLICATIONS

Barratt et al., "Self-calibrating Ultrasound-to-CT Bone Registration", Medical Image Computing and Computer-Assisted Intervention—MICCAI 2005, Lecture Notes in Computer Science vol. 3749, 2005, pp. 605-612.*

(Continued)

*Primary Examiner* — Katherine Fernandez
(74) *Attorney, Agent, or Firm* — Fay Kaplun & Marcin, LLP

(57) ABSTRACT

A bone registration system is disclosed. The bone registration system may have a device including a scanner arranged to scan a target surface area of bone to obtain scan data and a first communication component. The registration system may have also a first marker positionable on a first portion of bone. The first marker may include a second communication component arranged to transmit a location signal for indicating a position of the first marker in a plurality of dimensions relative to the device. The system may have also a registration unit that compares the scan data with surface data of the bone to generate position data identifying overlapping elements of the scan data relative to the surface data, determines location data from the location signal and determines a location of the first marker on a surface of the bone using the position data and the location data.

18 Claims, 6 Drawing Sheets

(51) Int. Cl.
*A61B 6/12* (2006.01)
*G06T 7/00* (2006.01)

(52) U.S. Cl.
CPC ........ *A61B 17/8866* (2013.01); *A61B 19/5244* (2013.01); *A61B 2019/5251* (2013.01); *A61B 2019/5263* (2013.01); *A61B 2019/5276* (2013.01); *A61B 2019/5287* (2013.01); *A61B 2019/5289* (2013.01); *A61B 2019/547* (2013.01); *A61B 2019/5416* (2013.01); *A61B 2019/5445* (2013.01); *A61B 2019/5454* (2013.01); *G06T 7/0024* (2013.01); *G06T 7/0028* (2013.01); *G06T 2207/30008* (2013.01)

(56) References Cited

U.S. PATENT DOCUMENTS

| | | | |
|---|---|---|---|
| 6,877,239 | B2 | 4/2005 | Leitner et al. |
| 7,244,234 | B2 | 7/2007 | Ridley et al. |
| 7,862,570 | B2 | 1/2011 | Russell et al. |
| 2002/0085681 | A1 | 7/2002 | Jensen |
| 2004/0152970 | A1* | 8/2004 | Hunter et al. ............ 600/424 |
| 2005/0124988 | A1 | 6/2005 | Terrill-Grisoni et al. |
| 2006/0015031 | A1* | 1/2006 | Kienzle, III ............ 600/424 |
| 2008/0013814 | A1 | 1/2008 | Carlsen |
| 2008/0147078 | A1* | 6/2008 | Francis et al. ............ 606/102 |
| 2010/0312247 | A1 | 12/2010 | Tuma |

FOREIGN PATENT DOCUMENTS

| | | |
|---|---|---|
| EP | 1925256 | 5/2008 |
| WO | 2004/046754 | 6/2004 |
| WO | 2010/025575 | 3/2010 |
| WO | 2010/111224 | 9/2010 |

OTHER PUBLICATIONS

Lavallee et al., "Computer-Assisted Spinal Surgery Using Anatomy-Based Registration", in: Computer-integrated Surgery: technology and clinical applications, eds. R.Taylor, et al., Boston, Massachusetts: Academic Press, 1996, pp. 425-449.*

Wein et al., "Automatic CT-ultrasound Registration for Diagnostic imaging and Image-Guided Intervention," Jun. 19, 2008, Medical Image Analysis, pp. 577-585.

Barratt et al. "Self-calibrating Ultrasound-to-CT Bone Registration", Medical Image Computing and Computer-Assisted Intervention—MICCAI 2005, Lecture Notes in Computer Science vol. 3749, 2005, pp. 605-612.

* cited by examiner

ULTRASOUND CT REGISTRATION FOR POSITIONING

PRIORITY CLAIM

The present application claims priority to U.S. Provisional Application Ser. No. 61/499,838 entitled "Ultrasound CT Registration for Positioning" filed on Jun. 22, 2011 and U.S. Provisional Application Ser. No. 61/499,849 entitled "Ultrasound CT Registration for Positioning" filed on Jun. 22, 2011, the entire disclosures of which are incorporated herein by reference.

BACKGROUND

CT (Computed Tomography) is often used to image bones as this permits the construction of high definition three-dimensional images. These high definition images facilitate understanding of fractures, ligament injuries and dislocations and assist in the formulation of treatment strategies. CT scanners, however, are large, bulky devices which are inconvenient for use during treatment procedures. Although ultrasound imaging devices are less bulky and more convenient for use during procedures, the images produced by these devices are less accurate and comprehensive than those produced by CT scanners.

SUMMARY OF THE INVENTION

The present invention relates to a bone registration system. The bone registration system may have a device including a scanner arranged to scan a target surface area of bone to obtain scan data and a first communication component. The registration system may have also a first marker positionable on a first portion of bone. The first marker may include a second communication component arranged to transmit a location signal for indicating a position of the first marker in a plurality of dimensions relative to the device. The system may have also a registration unit that compares the scan data with surface data of the bone to generate position data identifying overlapping elements of the scan data relative to the surface data, determines location data from the location signal and determines a location of the first marker on a surface of the bone using the position data and the location data.

DETAILED DESCRIPTION

Figure 1:
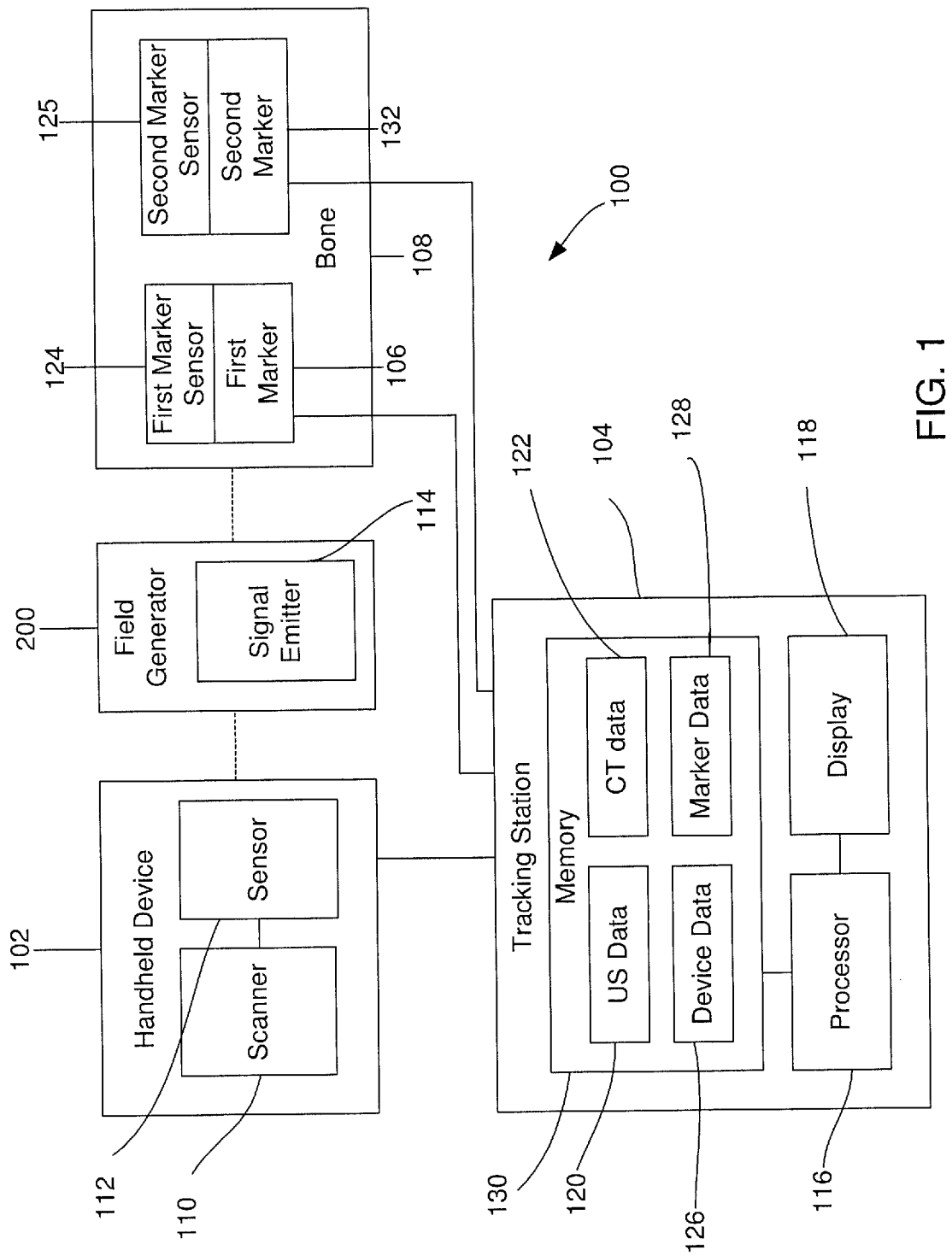
FIG. 1 shows a schematic drawing of a system according to a first exemplary embodiment of the present invention.

The present invention may be further understood with reference to the following description and the appended drawings, wherein like elements are referred to with the same reference numerals. The present invention relates to a system and method for registering a location of a bone marker on a bone for subsequent treatment of the bone. In particular, the present invention relates to a system and method for determining the relative locations of a handheld device and one or more markers to register the location of a marker on a bone with CT data of the bone. Once a position of the one or more marker on a bone is registered, during a treatment procedure, the movement of the marker may be tracked and the tracking information used to manipulate previously obtained CT image data to accurately track and display the position of one or more portions of bone during a procedure.

As will be described in greater detail hereinafter, the present invention is directed to a system and method for registering a location of the one or more markers positioned on the bone with the CT image data to aid in performing of a medical procedure (e.g., a bone fixation procedure, etc.). The exemplary system and method according to the invention permits the registration of the location of the one or more markers quickly and easily via an intra-operative procedure. Exemplary embodiments of the present invention describe a system and method utilizing a portable device to obtain data which is registered to establish the location of first and second markers on first and second portions of bone on a CT image so that, as the first portion of bone is manipulated during a treatment procedure, movement data may be used to manipulate the CT image to show the movement of the bone. It will be understood by those of skill in the art that although the exemplary embodiments describe first and second markers as positioned on first and second portions of a bone, respectively, the first and second markers may also be positioned on first and second bones that are adjacent to one another or on any other substantially rigid body structures so that a previously obtained CT image of the structures may be manipulated to show motion of the structures during a procedure.

As shown in FIG. 1, a system 100 according to an exemplary embodiment of the present invention comprises a handheld device 102 configured to obtain and transmit ultrasound data 120 (e.g., ultrasound image data) to a tracking system 104. The tracking system 104 registers the ultrasound data 120 with CT data 122 (e.g., a CT image) obtained prior to collection of the ultrasound data 120 to determine a location on the CT data 122 corresponding to the position of the handheld device 102 relative to the CT image, such as a bone, represented by the CT data 122. As would be understood by those skilled in the art, the handheld device 102 may use any known portable ultrasound imaging device including, for example, an ultrasound scanner 110 for obtaining ultrasound images. The handheld device 102 also has an electromagnetic sensor 112 for sensing an electromagnetic field emitted from a signal emitter 114 of a field generator 200. The electromagnetic signal emitter 114 generates an electromagnetic field that is also sensed by a first marker electromagnetic sensor 124 of a first marker 106. An electromagnetic sensor 112 of the handheld device 102 and the first marker sensor 124 communicate with the tracking system 104 by sending thereto device data 126 and marker data 128, respectively, in response to receiving the signal emitted by the signal emitter 114. The device data 126 and marker data 128 provide information on the locations of the device 102 and marker 106, respectively, relative to the field generator 200. The tracking system 104 uses the device and marker data 126, 128 to determine a position of the first marker 106 relative to the handheld device 102.

Using the collected information, the tracking system 104 registers (e.g., correlates) the ultrasound data 120 to the CT data 122 to identify the location of the handheld device 102 relative to, for example, a bone; registers the location of the handheld device 102 relative to the first marker 106, and determines a location of the first marker 106 on the image represented by the CT data 122, which may be shown on a display 118. In a further embodiment, the electromagnetic signal emitter 114 communicates with a second marker electromagnetic sensor 125 of a second marker 132 to determine the location of the second marker 132 relative to the handheld device 102 to determine a location of the second marker 132 relative to, for example, an image of a bone 108 represented by the CT data 122. Thus, in an embodiment where the first and second markers 106, 132 are located on first and second portions of a fragmented bone, the locations of the first and second markers 106, 132 on the bone may be registered prior to a manipulation of the fragments. Such registration may result in the first and second markers 106, 132 being used to track movement of the first and second portions of the bone relative to one another by manipulating the CT data 122 to display the motion by moving relative to one another portions of the image represented by the CT data 122 corresponding to the first and second portions of the bone 108. For example, the CT data 122 may be manipulated to show relative movement between the first and second portions of bone 108 on the display 118 based on the movement of the first and second markers 106, 132.

The scanner 110 of the handheld device 102 may take a 2D ultrasound image to obtain ultrasound data 120. The system 100 then looks through the ultrasound data 120 for portions bearing a similarity of contour to portions of the image represented by the CT data 122 to identify portions of the ultrasound data 120 and the CT data 122 which correspond to the same portion of the bone 108. The ultrasound data 120 and the CT data 122 may, however, have several points of similarity, requiring the handheld device 102 to take several 2D ultrasound images over discrete periods of time to ensure correct registration between these identified portions of data representing the same portion of the bone 108. The number of 2D ultrasound images required may depend, for example, on the homogeneity of the contour of the bone and the level of detail in the ultrasound and CT data 120, 122, respectively. For example, for long bones with large substantially homogeneous areas, more ultrasound scanning may be required to obtain the registration between the ultrasound and CT data 120, 122, respectively. Thus, several candidate locations of the CT data 122 may be identified and additional ultrasound data 120 (e.g., ultrasound images) collected until one of the several candidate locations is confirmed as correctly corresponding to a selected portion of the image represented by the CT data 122.

Figure 2:
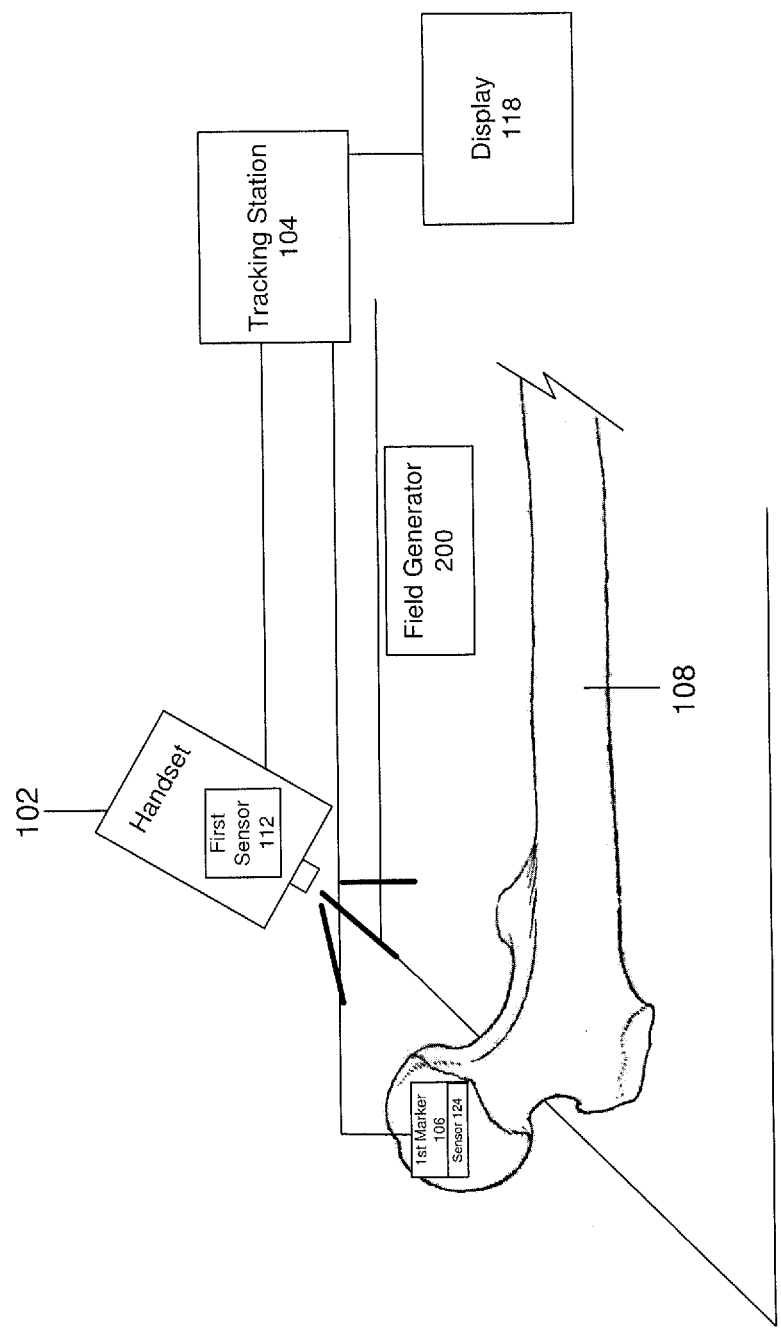
FIG. 2 shows a perspective view of the system according to the first exemplary embodiment of the present invention.

FIG. 2 depicts a use of the system 100 for registering the location of first and second markers 106, 132 on a bone 108 with a CT image of the bone 108. The electromagnetic sensor 112 provides device data 126, which includes a position and/or orientation of the handheld device 102 relative to the field generator 200. In particular, as would be understood by those skilled in the art, a known sensor may be employed as the sensor 112 to provide data on an angular orientation of the handheld device 102 in 6 dimensions, which includes first, second and third dimensions indicating a distance on X, Y and Z axes between the handheld device 102 and the field generator 200 and three dimensions relating to the angular rotation (i.e., Roll-Pitch-Yaw) of the handheld device 102 relative to the field generator 200. This device data 126 is similarly transmitted to the tracking station 104.

The electromagnetic signal emitter 114 of the field generator 200 communicates with the first electromagnetic sensor 124 and the tracking station 104 to provide marker data 128, which includes a position and/or orientation of the first marker 106 relative to the signal emitter 114. In particular, the signal emitter 114 emits a signal to the first marker electromagnetic sensor 124, which senses the position and/or orientation of the first marker 106 in 6 dimensions relative to the field generator 200. The 6 dimensions include 3 dimensions relating to a distance of the signal emitter 114 from the first marker electromagnetic sensor 124 along X, Y and Z axes and three dimensions relating to the angular rotation (i.e., Roll-Pitch-Yaw) of the signal emitter 114 relative to the first marker electromagnetic sensor 124. This marker data 128 is then transmitted to the tracking station 104.

The tracking station 104 may be a computer or other processing arrangement including a processor 116 and a display 118. The ultrasound data 120, CT data 122, device data 126 and marker data 128 may, for example, be saved to a memory 130 of the tracking station 104 and may be used to register the first marker 106 to the CT data 122. The processor 116 correlates the ultrasound data 120 and the CT data 122 to determine a position of the handheld device 102 relative to image of the bone 108 in the CT data 122. The processor 116 may then determine a location of the first marker 106 relative to the CT data 122 using the device data 126 and marker data 128. The location of the first marker 106 may also be displayed on the display 118. The processor 106 may register in real-time the ultrasound and CT data 120, 122, respectively, and determine the location of the first marker 106 on the image represented by the CT data 122 so that a system user may be provided with real-time information regarding completion of the registration process.

After registration of the first marker 106, a second marker 132 may be positioned on a second portion of the bone 108. Thus, when registration of the first marker 106 has been completed, the registration procedure discussed above may be repeated for the second marker 132 to register a location thereof. Once the locations of both the first and second markers 106, 132, respectively, have been determined relative to the CT data 122, relative movement between the first and second markers 106, 132 may be continuously tracked and monitored such that a manipulated CT image showing the relative movement of the first and second portions of the bone 108 may be displayed on the display 118 observable by a surgeon or other user to visualize the reduction of a fracture.

The embodiment depicted by FIGS. 1 and 2 has been described for a situation where the bone 108 in which the first and second markers 106, 132 are positioned is fractured. The fracture could result in two, three, four, etc., bone fragments in each of which a marker is positioned and its location subsequently registered so that at some point later the relative movement of the markers, and therefore the bone fragment associated with the marker, can be tracked on the CT image whilst the bone fragments are moved. An alternate use of the registration system 100 arises when a bone is in one piece, but it is to be divided by an osteotomy into two or more pieces. In this situation, the registered location of the first marker 106 can be used to identify and register the location of the second and each subsequent marker with the CT data by determining the locations of the second and subsequent markers relative to the first marker with reference to the registered location of the first marker 106.

Referring again to FIG. 2, a first exemplary technique utilizing the system 100 is shown. An electromagnetic field generator 200 emits an electromagnetic field capable of being sensed in the 6 dimensions described earlier. The electromagnetic field generator 200 comprises at least two coils (not shown). It is noted that although the embodiment of FIG. 2 is depicted with only the first marker 106 including a first sensor 124, the second marker 132 or any plurality of additional markers may be used without deviating from the scope of the invention. The handheld device 102 is connected to the tracking station 104 by, for example, a wired or wireless connection. The first marker 106 may also be connected to the tracking station 104 via a wired connection, although a wireless connection is also envisioned. The embodiment of FIG. 2 operates in a manner substantially similar to the mode of operation disclosed above. Specifically, a CT scan of the bone 108 is made and the CT data 122 is provided to the tracking system 104. The first marker 106 is positioned on a first portion of the bone 108 and the ultrasound seamier 110 is used to scan the first portion of the bone 108. It is noted that the position of the first marker 106 as depicted is exemplary only and that the first marker 106 may be positioned anywhere on the bone 108 without deviating from the scope of the invention. The ultrasound and device data 120, 126, respectively, along with marker data 128 for the first marker 106 is transmitted to the tracking station 104 and stored, for example, in a memory 130 and accessed via the processor 116 as required. The processor 116 compares and correlates the ultrasound and CT data 120, 122 to register the data—i.e., determine overlapping elements in the ultrasound and CT data 120, 122. Then, using the device data 126 which indicates a position of the handheld device 102 relative to the field generator 200 and the marker data 128, which indicates a location of the first marker 106 relative to the field generator 200, the processor 116 determines a location of the first marker 106 relative to the CT data 122. Specifically, the processor 116 identifies a position and orientation in 3D space relative to the field generator 200 of the first marker 106 to determine marker data 128, and the first sensor 112 of the handheld device 102 to determine device data 126. The processor 116 uses the marker data 128 and device data 126 to determine the relative location of the first marker 106 to the handheld device 102. The processor 116 uses also the ultrasound data 120 to link the location of the handheld device 102 to the CT data 122 to determine the relative location of the handheld device 102 to the bone 108 in the CT image. Knowing the location of the first marker 106 relative to the handheld device 102 and the location of the handheld device 102 relative to the CT image of the bone 108, the processor determines the location of the first marker 106 relative to the CT image of the bone 108 and thereby registers the location of the first marker 106 on the CT data 122 and, therefore, the bone 108. The relative location of the first marker 106 and the CT data 122 may be displayed on the display 118.

Once the first marker 106 has been registered relative to the CT data 122, the registration process may be repeated for any number of additional markers (not shown) using the same process as described for registering the first marker 106. For each additional marker, the ultrasound scanner 110 is used to scan that bone portion in which the bone marker to be registered is located. In this way, movement of a bone fragment during the registration procedure may be compensated. In the situation where the bone 108 is in one piece, a position of the second marker 132 may be detected relative to the first marker 106 to determine a location of the second marker 132 relative to the CT data 122. The relative location of the second marker 132 may also be displayed on the display 118. As those skilled in the art will understand, this relative registration process may be used in, for example, osteotomy procedures where the bone 108 is in one piece and the first marker communicates with the second marker to register a location thereof. It is noted, however, that for osteotomy procedures a user may also register the first and second markers individually with the tracking station 104.

In another embodiment of the invention, the registration process may be used for the treatment of scoliosis, with the first and second markers positioned on two different bones, e.g., vertebrae of the spine. In such an embodiment, the first and second markers are individually registered with the tracking station 104, as also described in greater detail earlier. Thus, once the locations of both the first and second markers 106, 132 have been determined, the user may move the first and second bones relative to one another and, consequently, move the first and second markers 106, 132, relative to one another. The motion between the first and second markers 106, 132 is used to manipulate the image represented by the CT data 122 so the movement between the first and second bones represented by the motion of the markers 106, 132 is shown on the display 118 so that a user may monitor movement of bones during treatment. The exemplary system and method according to the invention compensates for inadvertent movement of the bones or fragments since the location of the first and second markers 106, 132 is taken relative to the field generator 200 and not relative to a position thereof within the body. In yet another scoliosis fixation procedure, 3D ultrasound may be used bypassing the need for a build up a 3D image using slices of a 2D ultrasound image, as those skilled in the art will understand. A fixation procedure for a fractured bone may use a registration process substantially similar to that used for a scoliosis fixation procedure, with the first and second markers positioned on separate portions of the fractured bone.

In an exemplary embodiment, the handheld device 102 the ultrasound scanner may include a Siemens X150 for ultrasound scanning and a VF 10-5 vector transducer. The processor 116 may utilize the live MMGIFusion software developed by Princeton SCR for data acquisition and visualization and the IVUS (Interventional Ultrasound) software prototype developed at CAMP, Technical University of Munich and SCR, Princeton for automatic CT-Ultrasound registration. It will be understood by those of skill in the art, however, that this an exemplary embodiment only and that other systems may be utilized so long as they facilitate use of the system 100, as described above.

Figure 3:
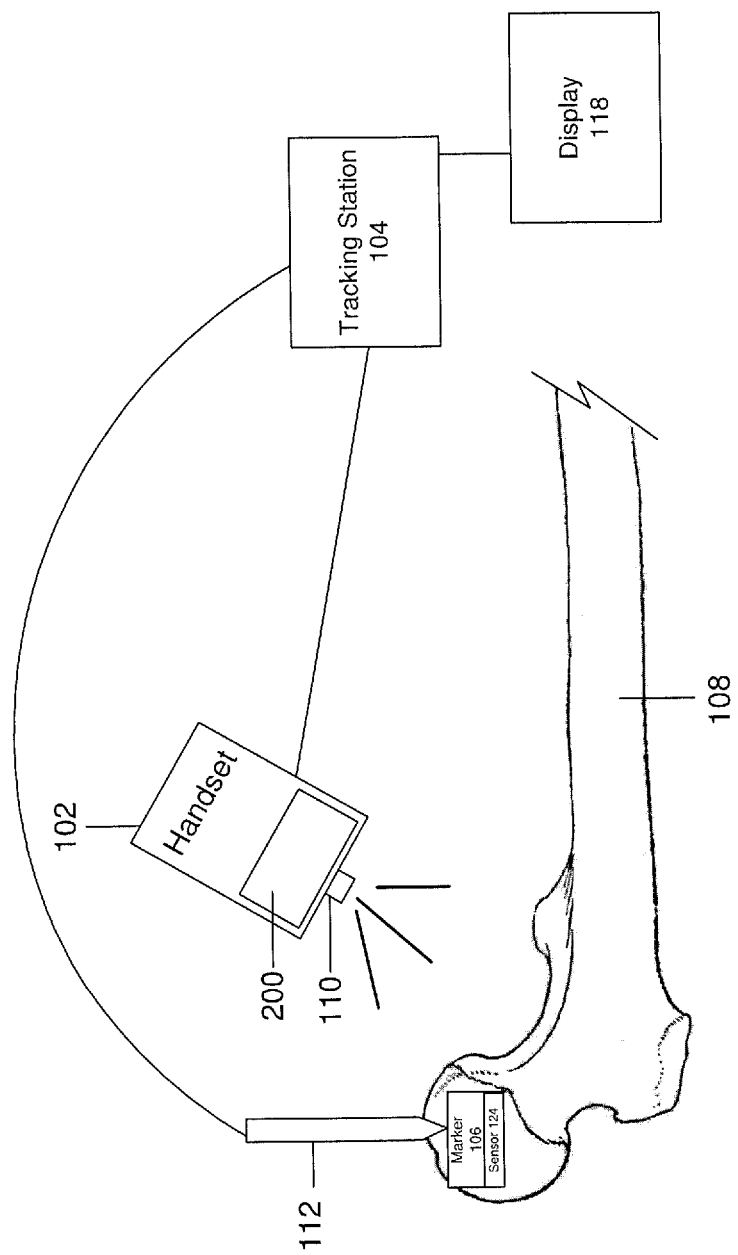
FIG. 3 shows a perspective view of a system according to a second exemplary embodiment of the present invention.
Figure 4:
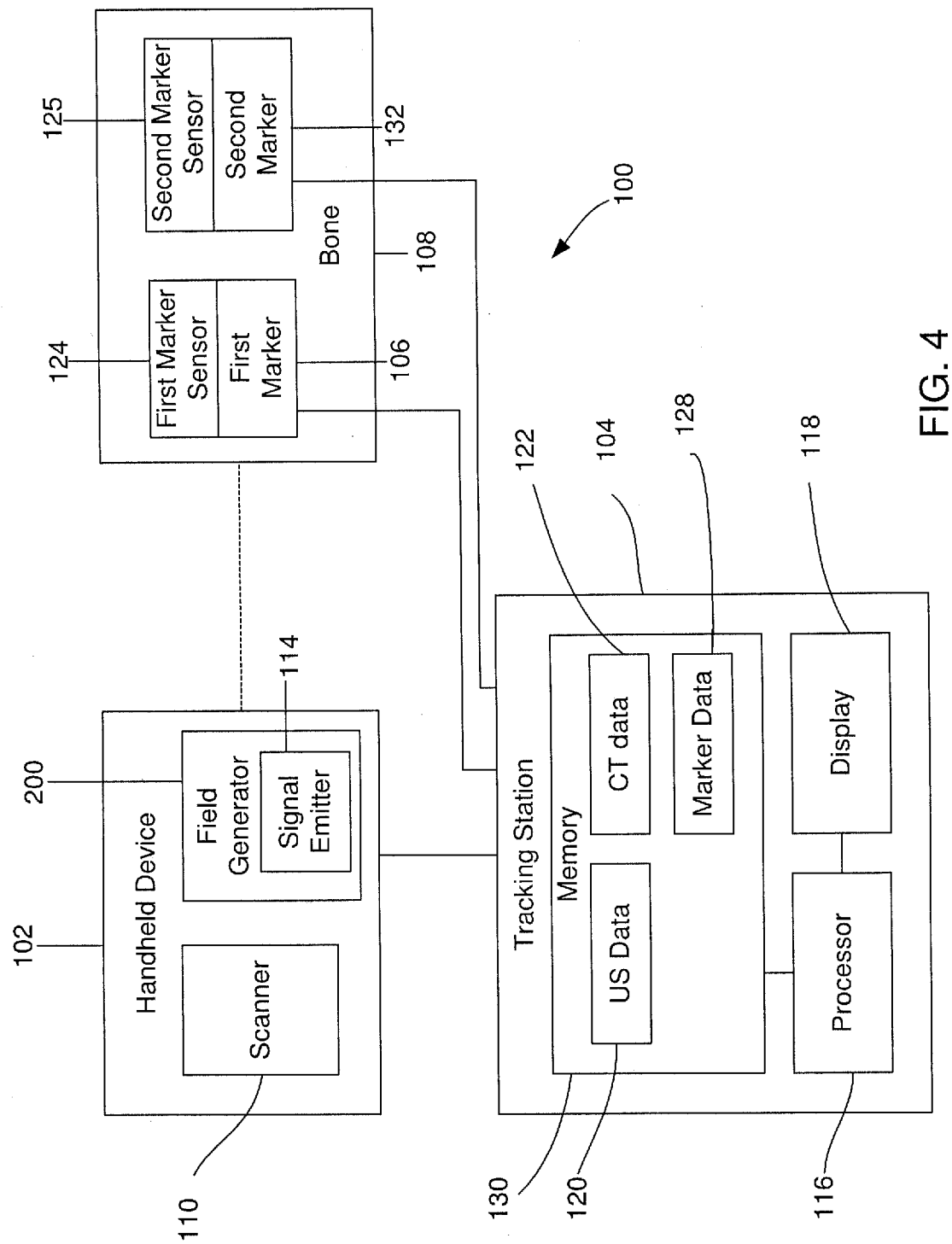
FIG. 4 shows a schematic drawing of the system according to the second exemplary embodiment of the present invention.

FIGS. 3-4 depict another exemplary marker registration system and method according to the invention. The system and method of FIGS. 3-4 includes a first marker 106 positionable on the bone 108 including a first marker electromagnetic sensor 124. In this embodiment the field generator 200 is located on the handheld device 102. The handheld device 102 and first marker electromagnetic sensor 124 are connected to the tracking station 104 by a wired or wireless connection. The system and method of FIG. 3 operates similarly to that disclosed above with respect to FIGS. 1 and 2. However, since the field generator 200 is located on the handheld device 102, the position and orientation in 6 dimensions of the first marker 106 relative to the field generator 200 provides the processor 116 with the marker data 128. For the system of FIGS. 3-4, the processor 116 can register the location of one or more markers without a first sensor associated with the handheld device 102 and device data 126. Specifically, the first marker electromagnetic sensor 124 provides marker data 128 including a position and/or orientation of the first marker 106 relative to the handheld device 102, compares the ultrasound data 120 to the CT data 122 and registers a position and/or orientation of the handheld device 102 relative to the CT image of the bone 108. The marker data 128 and the registered location of the handheld device 102 is then used to register a location of the first marker 106 on the image represented by the CT data 122 by correlating marker data with the registered location of the handheld device 102 relative to the CT image of the bone 108.

Figure 5:
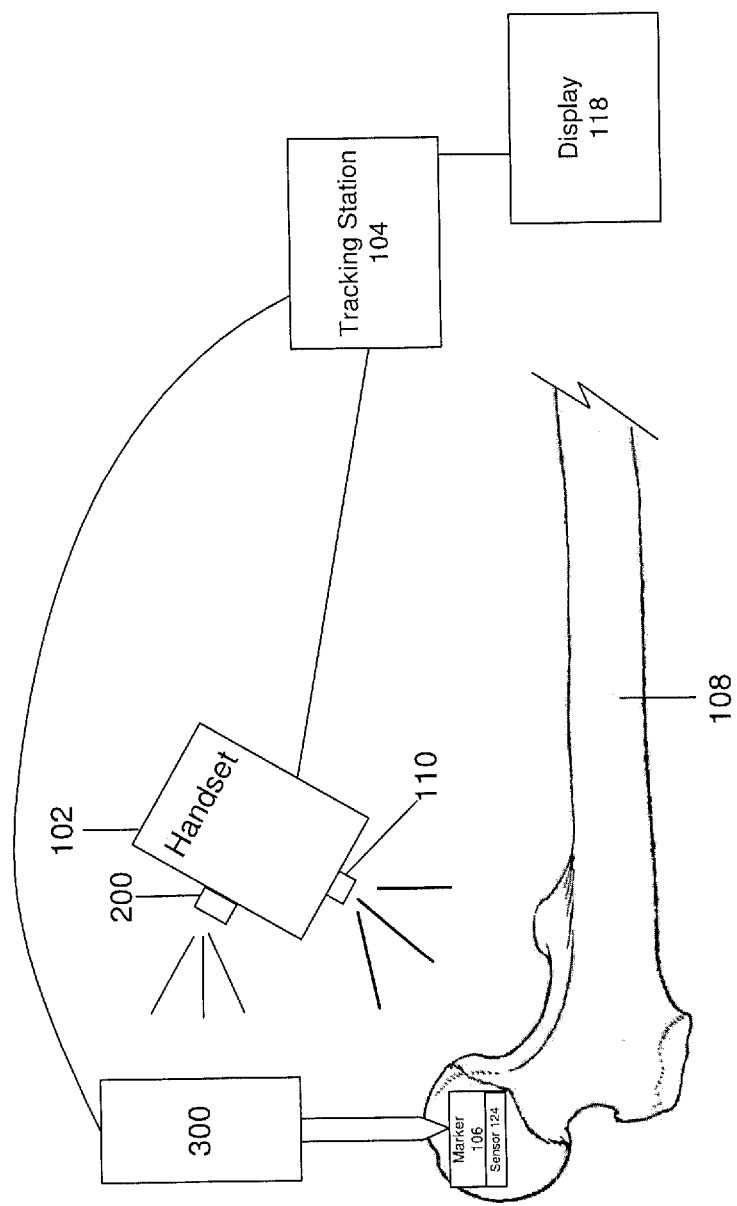
FIG. 5 shows a perspective view of a system according to a third exemplary embodiment of the present invention.
Figure 6:
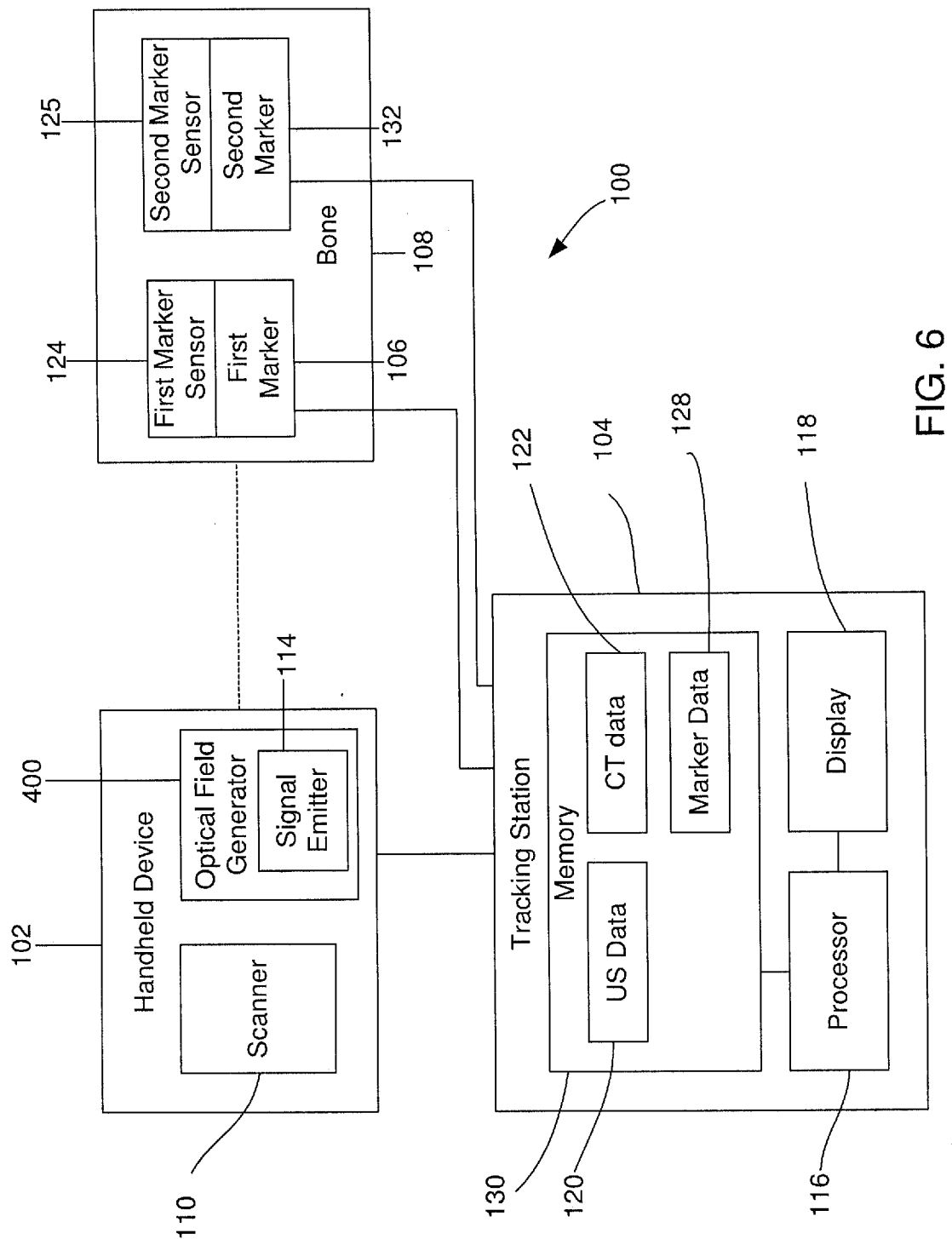
FIG. 6 shows a schematic drawing of the system according to the third exemplary embodiment of the present invention.

FIGS. 5-6 depict a system and method according to another embodiment of the invention. The system and method are substantially the same as described for FIGS. 3-4 with the exception that field generator 200 is replaced with an optical field generator 400 (e.g., light emitting array). Specifically, the handset 102 may communicate with an optical tracking instrument 300 connected to the first marker 106. The optical tracking instrument 300 aids in location and registration of the first marker 106 with the tracking station 104 in accordance with the method described with respect to the embodiment depicted by FIGS. 3-4.

It will be apparent to those skilled in the art that various modifications and variations can be made in the structure and the methodology of the present invention, without departing from the spirit or the scope of the invention. Thus, it is intended that the present invention come within the scope of the appended claims and their equivalents.

What is claimed is:

1. A bone registration system, comprising:
   a device including a scanner arranged to scan a target surface area of bone to obtain scan data and a first communication component configured to transmit a first location signal for indicating a position of the device;
   a first marker adapted to be positioned on a first portion of the bone, the first marker including a second communication component configured to transmit a second location signal for indicating a position of the first marker in a plurality of dimensions relative to the device;
   a processor configured to compare the scan data with stored surface data of the bone to generate position data identifying overlapping elements of the scan data relative to the surface data, to determine location data from the first and second location signals and to determine a location of the first marker relative to a surface of the bone in the surface data using the position data and the location data; and
   a second marker adapted to be positioned on a second portion of the bone, wherein the first and second markers are configured to communicate with one another to determine relative marker data including a position of the first marker relative to the second marker, wherein the processor is further configured to process the relative marker data to determine a location of the second marker relative to the surface of the bone in the surface data.

2. The system of claim 1, wherein the scan data is ultrasound data and the surface data is CT data.

3. The system of claim 1, further comprising a signal generator configured to generate a reference signal;
   wherein the first and second communication components are a first sensor and a second sensor, each configured to sense the reference signal and transmit respective location signals to the processor indicating a position of the respective communication component in a plurality of dimensions relative to the signal generator; and
   wherein the processor determines location data from the location signals to indicate the position of the first marker relative to the device in a plurality of dimensions.

4. The system of claim 3, wherein the reference signal is an electromagnetic signal.

5. The system of claim 1, wherein
   the first communication component is a signal generator configured to generate a reference signal; and
   the second communication component is a sensor configured to sense the reference signal and transmit the second location signal to the processor for indicating a position of the first marker relative to the device in a plurality of dimensions.

6. The system of claim 5, wherein the signal generator and the sensor are one of electromagnetic and optical.

7. The system of claim 1, wherein the location data indicates a position of the first marker relative to the device in six dimensions.

8. The system of claim 1, wherein respective locations of the first and second markers on the surface of the bone are identifiable using the device.

9. The system of claim 1, further comprising a display showing the location of the first marker relative to the surface of the bone in the surface data.

10. The system of claim 1, wherein the second marker includes a third communication component communicating with the first communication component to determine location data indicating a position of the first communication component relative to the third communication component in a plurality of dimensions.

11. The system of claim 1, wherein the device includes one of an electromagnetic field generator and an optical field generator.

12. A method for bone registration, comprising:
   scanning a target surface area of bone to obtain scan data using a device including a scanner and a first communication component configured to transmit a first location signal for indicating a position of the device;
   positioning a first marker on a first portion of the bone, the first marker including a second communication component configured to transmit a second location signal indicating a position of the first communication component relative to the second communication component in a plurality of dimensions;
   positioning a second marker on a second portion of the bone;
   comparing, using a processor, the scan data with stored surface data of the bone to generate position data identifying overlapping elements of the scan data relative to the surface data, determining location data from the first and second location signals and determining a location of the first marker relative to a surface of the bone in the surface data using the position data and the location data;
   determining relative marker data indicating a position of the first marker relative to the second marker; and
   processing the relative marker data to determine a location of the second marker relative to the surface of the bone in the surface data.

13. The method of claim 12, wherein the scan data is ultrasound data and the surface data is CT data.

14. The method of claim 12, wherein the first communication component is an electromagnetic signal emitter and the second communication component is an electromagnetic sensor.

15. The method of claim 12, wherein the location data indicates a position of the device relative to the first marker in six dimensions.

16. The method of claim 12, wherein the second portion of the bone has a fixed spatial relationship with the first portion of the bone.

17. The method of claim 12, wherein the second portion of the bone has a non-fixed spatial relationship with the first portion of the bone.

18. The method of claim 12, further comprising:
   displaying the location of the first marker relative to the surface of the bone in the surface data on a display.

* * * * *